United States Patent
Ostrom et al.

(10) Patent No.: US 6,488,644 B1
(45) Date of Patent: Dec. 3, 2002

(54) COUPLING AND ORTHOTIC BRACE INCORPORATING THE COUPLING

(75) Inventors: Devin J. Ostrom; Ivan D. Samila; Stephen Naumann, all of Toronto (CA)

(73) Assignee: Becker Orthopedic Appliance Company, Inc., Troy, MI (US)

( * ) Notice: Subject to any disclaimer, the term of this patent is extended or adjusted under 35 U.S.C. 154(b) by 0 days.

(21) Appl. No.: 09/338,814

(22) Filed: Jun. 23, 1999

(30) Foreign Application Priority Data

Jun. 23, 1998 (CA) .............................................. 2241575

(51) Int. Cl.$^7$ ................................................. A61F 5/00
(52) U.S. Cl. .............................. 602/16; 602/23; 602/20; 403/87
(58) Field of Search ............................... 602/5, 16, 20, 602/23, 26, 27; 403/56, 87, 127; 623/45, 48

(56) References Cited

U.S. PATENT DOCUMENTS

| | | | |
|---|---|---|---|
| 3,414,908 A | * 12/1968 | Waggott et al. ............... | 623/38 |
| 3,671,978 A | * 6/1972 | May ............................. | 623/38 |
| 3,699,954 A | 10/1972 | Craig | |
| 3,815,589 A | 6/1974 | Bosley | |
| 4,108,168 A | 8/1978 | Craig | |
| 4,203,433 A | 5/1980 | Prahl | |
| 4,497,315 A | 2/1985 | Fettweis et al. | |
| 4,574,790 A | 3/1986 | Wellershaus | |
| 4,576,151 A | 3/1986 | Carmichael et al. | |
| 4,881,532 A | 11/1989 | Borig et al. | |
| 4,901,710 A | 2/1990 | Meyer | |
| 4,913,136 A | 4/1990 | Chong et al. | |
| 5,086,760 A | * 2/1992 | Neumann et al. ......... | 602/16 X |
| 5,147,286 A | 9/1992 | Meals | |
| 5,344,391 A | 9/1994 | Modglin | |
| 5,421,810 A | * 6/1995 | Davis et al. ................. | 602/16 |
| 5,470,310 A | * 11/1995 | Sutcliffe ..................... | 602/24 |
| 5,507,818 A | * 4/1996 | McLauglin .................. | 623/18 |
| 5,620,412 A | 4/1997 | Modglin | |
| 5,681,267 A | 10/1997 | Molino et al. | |
| 5,681,270 A | 10/1997 | Klearman et al. | |
| 6,027,466 A | * 2/2000 | Diefenbacher et al. ....... | 602/16 |
| 6,090,057 A | * 7/2000 | Collins et al. ................ | 602/16 |
| 6,254,559 B1 | * 7/2001 | Tyrrell ......................... | 602/16 |

OTHER PUBLICATIONS

Sage, "Cerebral Palsy" Campbell's Operative Orthopaedics. C.V. Mosby Company: Torono, vol. 4, 7th Ed., 1987, pp 2843–2855, pp 2891–2907, pp 2914–2923.

(List continued on next page.)

*Primary Examiner*—Denise M. Pothier
(74) *Attorney, Agent, or Firm*—Ryndak & Suri

(57) ABSTRACT

A coupling, for example, for an orthotic brace has a cam member with a first planar bearing face journalled for rotation on a planar bearing surface of a first coupling portion, and a second planar bearing face inclined to the first face and journalled to rotate relative to a planar bearing surface of a second coupling portion. A clamping device urges the faces and surfaces together to exert a frictional reaction retaining the cam member in a selected rotational position and retains the coupling portions rigidly opposed towards the cam member.

36 Claims, 3 Drawing Sheets

OTHER PUBLICATIONS

Meehan, et al., "The Scottish Rite Abduction Orthosis for the Treatment of Legg–Perthes Disease," The Journal of Bone and Joint Surgery, vol. 74–A, No. 1, Jan. 1992, pp 2–11.

Tachdjian, "Plate 114, Adductor Myotomy of the Hip. Gracilis Myotomy and Section of the Psoas Tendon at its Insertion," pp. 564–569; "Plate 115, Recession (Musculotendinous Lengthening) of the Psoas Tendon at the Pelvic Brim (Carroll Technique)," pp. 570–573, Atlas of Pediatric Orthopaedic Surgery, vol. 1, W.B. Sanders Company: Toronto 1994.

Wenger, "Developmental Dysplasia of the Hip," pp. 256–258 and 278–280; Rang, "Neuromuscular Disease," pp 534–536, pp 544, 549–562, The Art and Practice of Children's Orthopaedics. Raven Press: New York 1993.

Staff, NYU Post–Grad. Medical School, "Lower–Limb Orthotics," Prosthetics and Othotics Department, New York University Post–Graduate Medical School: New York, 1981 Rev., Aug. 1981, pp 135–137, pp 148–152.

* cited by examiner

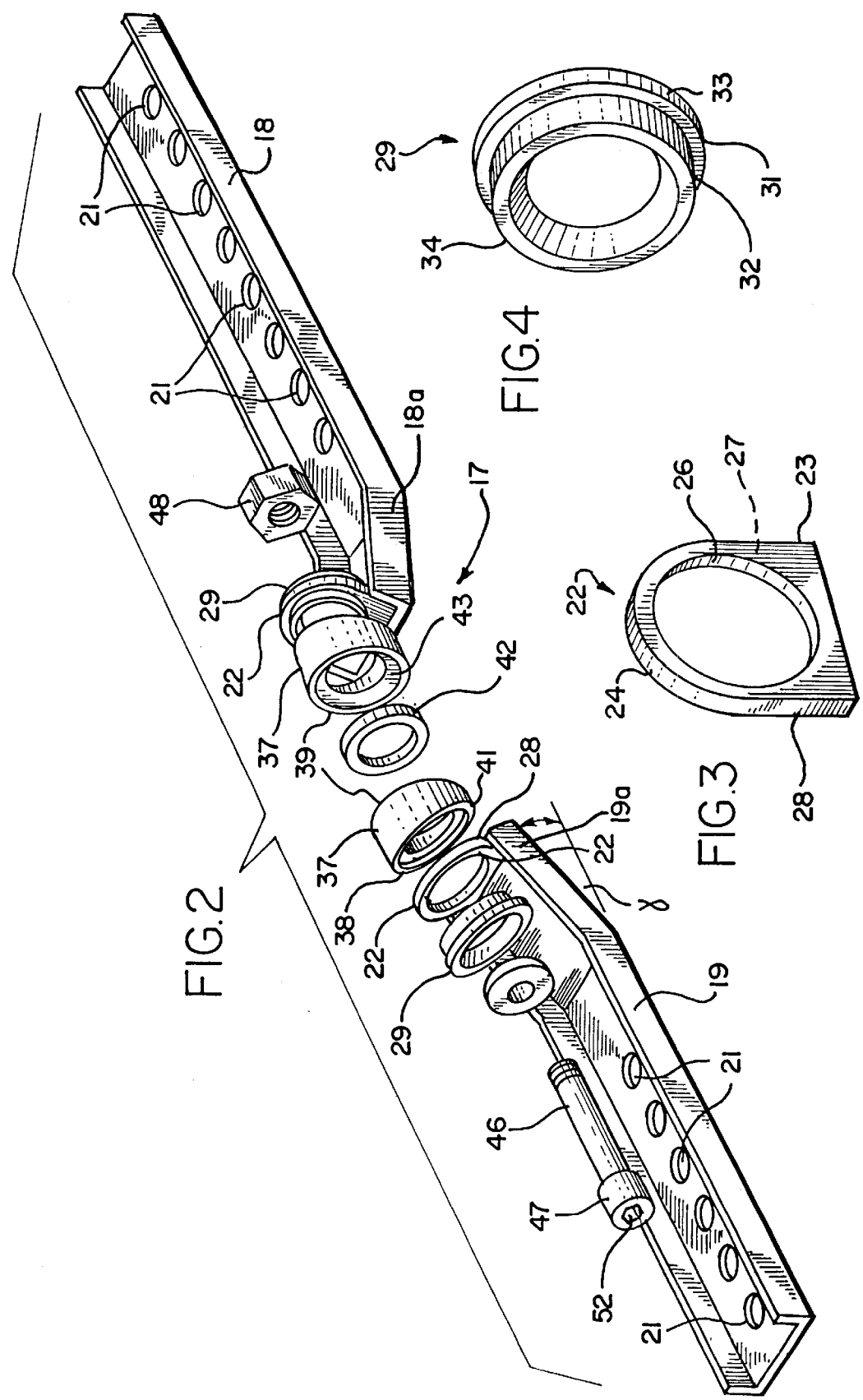

COUPLING AND ORTHOTIC BRACE INCORPORATING THE COUPLING

FIELD OF THE INVENTION

The present invention relates to a coupling and more particularly although not exclusively to a coupling for use in an orthotic brace, for example, a hip, is shoulder, wrist or ankle brace.

BACKGROUND OF THE INVENTION

Known couplings of which the applicants are aware have not been as strong and rigid or as durable as may be considered desirable. For example, known ball and socket couplings that rely on set screws engaging the surface of the ball to locate the portions of the coupling are prone to slippage under bending stress, while the set screws deform and pit the surface of the ball and ultimately render it unserviceable.

SUMMARY OF THE INVENTION

In one aspect, the invention provides a coupling comprising first and second portions each comprising a planar bearing surface, a cam member having a first planar bearing face bearing rotationally on the planar bearing surface of the first portion and journalled thereto through a first journal bearing resisting lateral slippage, a second planar bearing face disposed in a plane inclined to the plane of the first bearing face and bearing rotationally toward the planar bearing surfaces of the second portion and journalled thereto through a second journal bearing resisting lateral slippage, and a clamping device urging said bearing surface toward said bearing faces of the cam member and generating a frictional reaction retaining each bearing surface in a selected rotational position with respect to the cam member.

Since the compressive forces are transmitted through opposing planar faces, great compressive stress can be applied and hence high frictional forces generated without permanently deforming the coupling elements. This provides a coupling of greatly improved strength characteristics. Further, the wedge-like cam member together with the slippage resistant journal bearings provide in effect a monolithic body in the clamped condition of the coupling, so as to provide a coupling with excellent rigidity and resistance to bending.

BRIEF DESCRIPTION OF THE DRAWINGS

In the accompanying drawings

FIG. 2 is an isometric view of the coupling in disassembled or exploded condition.

FIGS. 3 to 8 show isometric or side views of elements of the coupling.

DETAILED DESCRIPTION OF THE INVENTION

Figure 1:
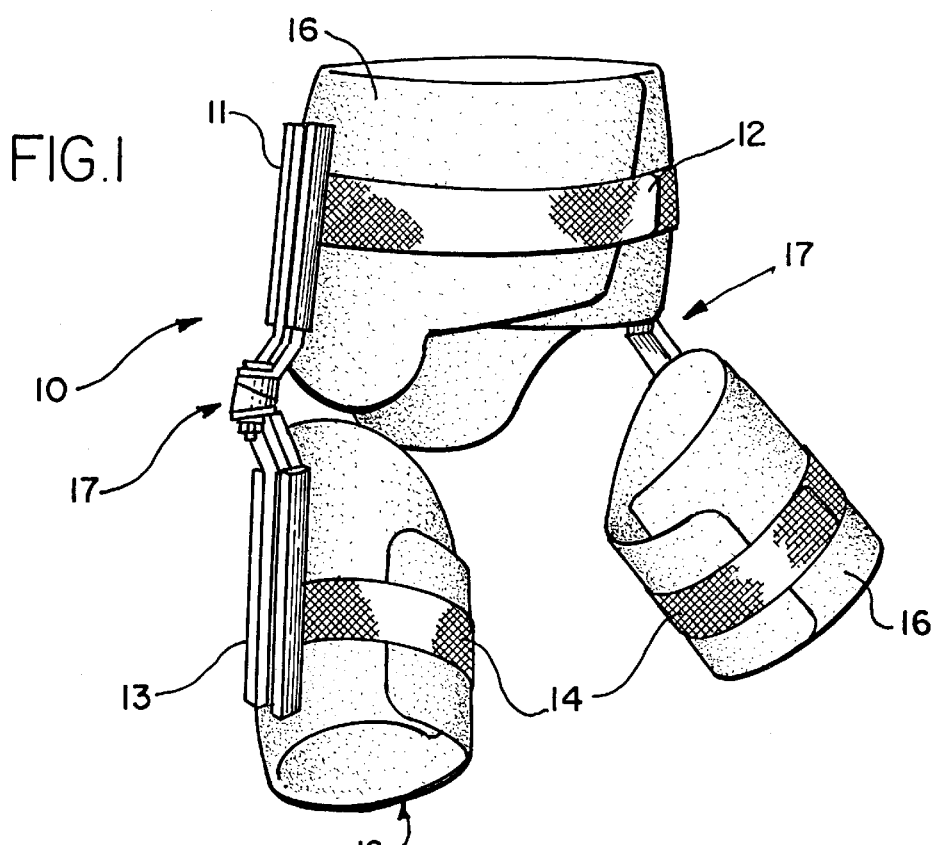
FIG. 1 shows an example of a brace incorporating a coupling in accordance with the invention.

With reference to the accompanying drawings, FIG. 1 shows an example of a brace in accordance with the invention, and, more specifically, a hip abductor brace 10, comprising a first generally channel shaped rigid brace portion 11 adapted to be applied to the rear of the hips of the patient and to be secured to the patient by straps 12. Typically the straps 12 may be provided with hook and loop type fasteners (trademark VELCRO) for fastening them together. The brace 10 further comprises two rigid generally channel shaped second brace portions 13 adapted to be applied to the thighs of the patient and similarly provided with straps 14 for securing the brace portions 13 to the thighs.

The portions 11 and 13 may also be provided with resilient cushioning pads 16 that are interposed between the patient's body and the brace portions 11 or 13 and the straps 12 and 14 in order to increase the wearing comfort of the device for the patient.

Each second portion 13 is connected to the main portion 11 through an adjustable coupling 17 shown in more detail in FIG. 2.

The coupling comprises first and second support arms 18 and 19 that are connected to the portions 11 and 13, respectively. Preferably, as shown, the arms 18 and 19 are of channel section for increased strength and rigidity. Desirably, the arms 18 and 19 are connected to the portions 11 and 13 in such manner that they are longitudinally adjustable with respect thereto, in order to allow adjustment of the longitudinal spacing between the first and second portions 11 and 13. In the example illustrated, each arm 18 and 19 is formed with a series of holes 21. Each portion 11 and 13 may be formed with two or more similar holes that can be aligned with two or more holes selected from the holes 21 and connected thereto by conventional releasable fasteners.

The end of each arm 18 and 19 remote from the portion 11 or 13 is connected to, for example by welding, or is formed integrally with, a collar 22 shown in more detail in FIG. 3. In the example seen in FIG. 3, the collar 22 comprises a rectangular base portion 23 that fits snugly with the channel of the arm 18 or 19 and is welded thereto, and an upper portion, preferably with a smoothly curved upper side 24. A circular aperture 26 is formed through the collar 22.

The opposing inner face 28 and outer face 27 of the collar 22 are planar, and, in the preferred form, are parallel to one another.

Figures 5, 6, 7, 8:
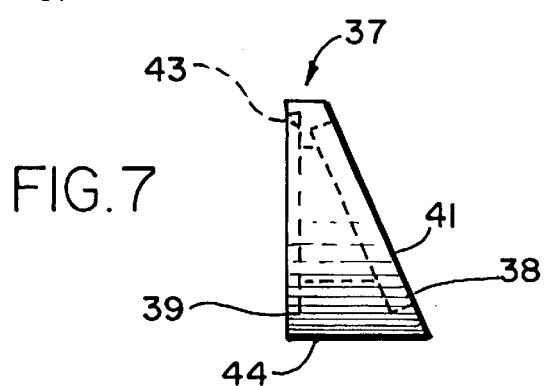

A generally cylindrical bushing 29 as seen in FIGS. 4 and 5 is received within each aperture 26. The bushing 29 comprises a circular outer portion 31 that may be formed on one side with a flat 32 to accommodate the base of the channel in the arms 18 or 19. The outer portion 31 has an annular inner face 33 that preferably extends at right angles to the axis of the bushing 29.

An inner cylindrical stub portion 34 has a diameter smaller than portion 31 and fits snugly within the aperture 26 in the collar 22. The bushing 29 has a circular opening through it defined by a generally inwardly tapering and more preferably conical outer bore 35 and an inner bore 36 that generally tapers outwardly and is preferably conical outwardly from the inner end of the stub portion 34.

In the assembled condition, a wedge shaped cam member 37, as shown in more detail in FIGS. 6 and 7, is journalled on the stub portion 34 and engages rotationally on the inner face 28 of the collar 22.

As seen in the drawings, the cam member 37 is preferably cylindrical, and has a continuous outer planar bearing face 38 that preferably is inclined to the axis of the member 37, and hence is generally elliptical, and a continuous inner planar bearing face 39 disposed in a plane inclined to the plane of the outer face 38, and preferably at right angles to the axis of the member 37, and hence is preferably annular.

The outer face 38 of the cam member 37 is formed with a cylindrical recess 41 with its axis at right angles to the face 38 of diameter such that it snugly receives the outside diameter of the stub 34 so that the cam 37 is journalled for rotation on the stub 34 and the engagement between the stub 34 and the recess 41 prevents transverse slippage of the cam member 37 relative to the bushing 29 and hence relative to the collar 22 and arm 18 or 19 with respect to which the bushing 29 is retained laterally against slippage by virtue of its snug engagement in the aperture 26.

The depth of the recess 41 is sufficient that a clearance is retained between the continuous land at its base and the inner end of the stub 34, so that the stub 34 does not space the member 37 from the collar inner face 28.

In the example illustrated, two cam members 37 are employed having their inner bearing faces 39 journalled together through interposition of a cylindrical washer 42 of a diameter to fit snugly within a cylindrical recess 43 formed at right angles in each inner annular face 39. The depth of the recess 43 is again sufficient that in the assembled condition there is a slight axial clearance between an end of the washer 42 and the annular inner end of the recess 43 so that the faces 39 can be placed in contact with one another and are not spaced apart by the washer 42.

A cylindrical bore 44 passes through each cam member 37 between the recesses 41 and 43.

In the assembled condition of the coupling, a releasable clamping device exerts compressive force between the outer sides of the bushings 29. In the preferred form, as seen in the drawings, the clamping device comprises a tensile member, for example, a threaded stud 46 passed through the bushings 29, collars 22, cam members 37 and washer 42.

Figure 9:
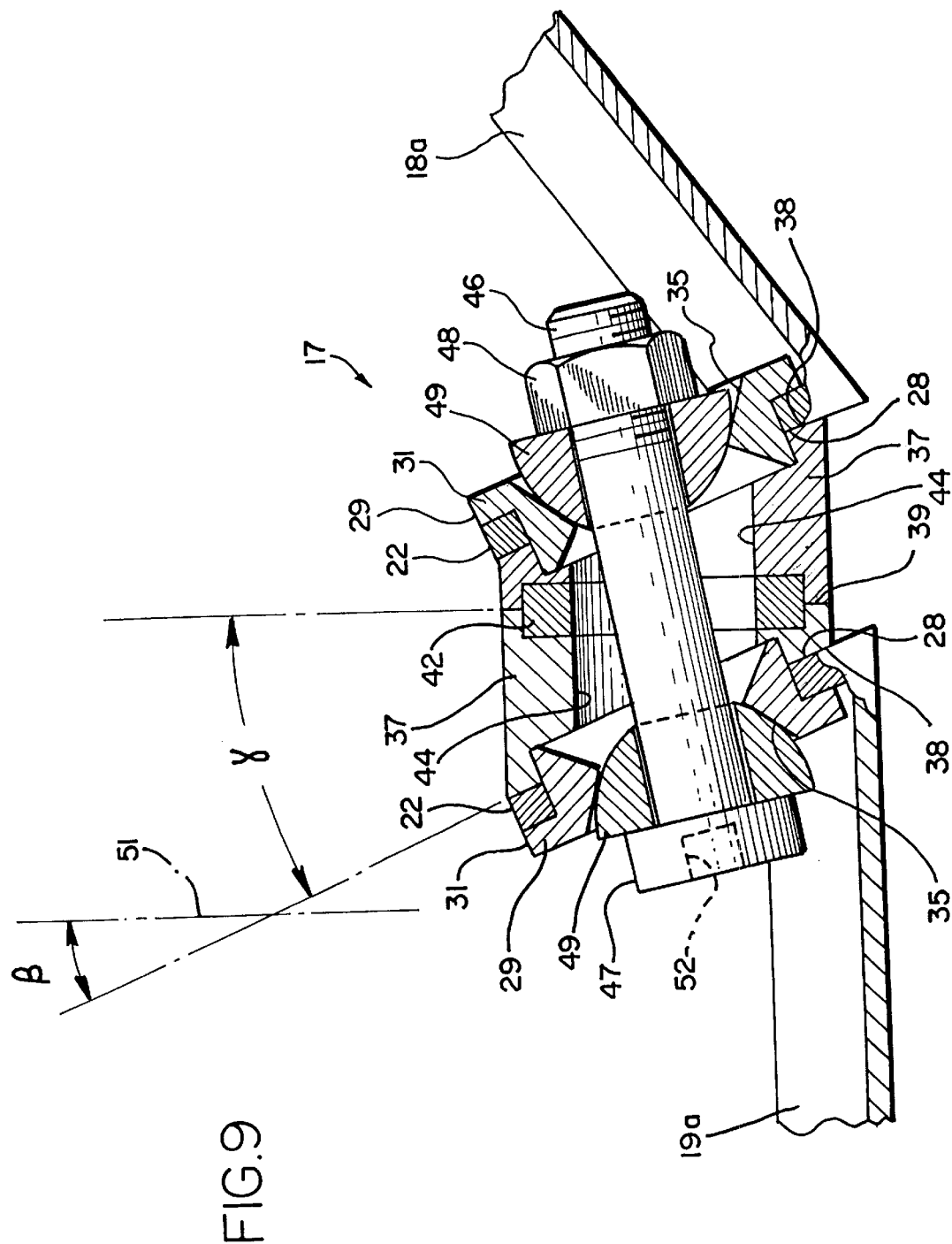
FIG. 9 is a partially schematic side view partially in section of the coupling in assembled condition.

In the example illustrated, one end of the threaded stud 46 is provided with an enlarged head 47 and a nut 48, preferably a locknut, is threaded on the opposite end. Preferably a convexly contoured, and more preferably part spherical, for example, hemispherical, washer 49 that fits snugly on the shaft of the stud 46 is interposed between each bushing 29 and effective portion of the clamping device, in this case the head 47 or nut 48, so that the washer 49 bears on the tapering side of the bore 35 and distributes the compressive stress applied by the clamping device evenly over the area of contact between the washer 49 and bushing 29, so as to resist a tendency for the washer 49 and bushing 29 to become permanently deformed when compressive force is applied. This stress distribution is preserved at the various angles of inclination that the stud 46 or other clamping device may adopt relative the axes of the bushings 29 in use. In the example illustrated, as will be appreciated from consideration of FIG. 9, the washer 49 contacts the tapering bore 35 along a generally annular zone.

In use, with the clamping device in a released condition, by swiveling one cam member 37 about its journal bearing relative to an adjacent arm, for example, arm 18, and, if necessary, swiveling the other cam member 37 about its journal bearings relative to the first-mentioned cam member 37 and relative to its adjacent arm 19, the arms 18 and 19 can be adjusted through a range of angles and rotational positions relative to one another. As each cam member 37 rotates, the inner face 28 of the adjacent collar provides a continuous planar bearing face, generally annular, on which the cam bearing face 38 rotates.

As the relative angles and positions of the axes of the arms 18 and 19 are adjusted, the angle and position of each end of the clamping device such as stud 46 and hence of the washers 49, varies relative to the collars 22 and bushings 29, so that the washers 49 swivel within the bores 35 on which they bear, and, as mentioned above, bear at an annular zone of contact with the bushings 29.

Once the arms 18 and 19 have been set at a desired relative angle and position, the clamping device is tightened, for example, the nut 48 is tightened up by rotation relative to the threaded stud 46. The head 47 may have a socket 52 to receive a hex or like key to assist in locating the stud 46 to facilitate rotation relative to the nut. When the coupling is fully tightened, the collars 22 are compressively gripped between the outer portions 31 of the adjacent bushings 29 and the outer bearing faces of the cam members 37. Since the compressive forces between the bushings 29 and collars 22, between the collars 22 and the adjacent outer bearing faces 38 of the cam members 37 and between the inner opposing bearing faces 39 are borne by opposing planar faces, great compressive stress can be applied without risk of permanent deformation of the material from which the coupling elements are made. As a result, great frictional reaction between the interengaging elements can be derived, so that, once fully tightened up the coupling is highly resistant to dislocation or displacement. Further, as will be appreciated from consideration of, for example, FIG. 9, once the coupling is tightened up the wedge-like cam members 37 form, in effect, a monolithic block between the inner faces of the collars 22, since the journalling stubs 34 and washer 42 prevent relative lateral shifting or slippage of the journalled elements, while the outer portion 31 of the bushings 29 tightly engage the outer faces of the collars 22, and the stubs 34 prevent lateral shifting of the collars 22, so that the joint, once secured, is of great strength and rigidity.

Considering each cam member 37 individually, the inner face 39 of the member 37, in the clamped position of the coupling, bears toward the opposing collar 22, while the other cam member 37, and the washer 42, form part of a journal bearing journalling the member 37 for rotation relative to the collar 22.

An advantage of the coupling as described is that it is adapted to be formed of inert non-corrodible materials, so that the coupling can be readily disassembled, cleaned and sterilized, for example, by autoclaving. Merely by way of example, the arms 18, 19, collars 22, stud 46 and nut 48 may be stainless steel and the bushings 29, cam members 37, and washers 42 and 49 may be aluminum, for example, anodized aluminum.

The structural portions of the brace portions 11 and 13 may be molded from readily cleanable and sterilizable plastics, for example, polyethylene and polyethylene/polypropylene copolymers.

Each arm 18 and 19 may have its collar 22 connected on an end portion 18a or 19a that is inclined with respect to the general plane of the main portion of the arm 18 or 19. This provides further freedom of adjustment of the angles of the arms 18 or 19 relative to one another, since, as will be appreciated, the arms 18 and 19 may be rotated relative to the coupling 17 so that they extend parallel to one another or at extreme angles relative to one another. Further, the angled portions 18a and 19a facilitate access to head 47 and nut 48 to facilitate loosening and tightening of the nut 48 relative to the stud 46.

Further, preferably each collar 22 is inclined with respect to a plane normal to the general plane of the end portion 18a or 19a on which it is connected. As will be appreciated, this provides further freedom of angular adjustment.

In one preferred form, merely by way of example, the angle a between each arm portion 18a or 19a and the main arm 18 or 19, and the angle P between the collar 22 and a plane 51 extending normal to the general plane of the arm portion 18a or 19a are each about 11.25°, and the angle γ between bearing faces 38 and 39 of each cam member is about 22½°. As will be appreciated, this allows the angle between arms 18 and 19 to be varied between 0 and 90°. These angles are merely by way of illustration and smaller or greater angles may be employed. However, if the angles between the faces 38 and 39 are excessively large, problems may tend to occur if the stud 46 tends to bind on the sides of the bore 44 during swiveling adjustment. Preferably, angles α and β are each between 0 and about 30° and more preferably about 5 to about 15° and angle γ is preferably about 5 to about 35°, more preferably about 10 to about 30°.

Preferably, the bearing faces 39 of the cam members 37 that are in contact are at right angles to axes of the members 37 to provide increased stability in the clamped condition and so that, in the case in which an internal stud 46 is employed, the bores 44 remain coaxial and in alignment at all rotational positions, to reduce problems of the stud 46 binding on the inner side of a bore 44.

Various other modifications may be made. If desired, the coupling may have only one cam member 37 having a bearing face 39 journalled direct to a collar 22. The coupling may have three or more cam members 37 journalled in series to one another and to the collar 22 at opposite ends of the series.

In the preferred form, for ease of manufacture, the cam members 37 are similar to one another. However, one cam member 37 may have the angle between its inner and outer faces different from that of the other cam member 37. Instead of using a washer 42 to journal the cam members 37 together, one cam member 37 may be formed integrally with a projecting annular collar on an inner face 39 received snugly in an annular recess within the inner face 39 of the other cam member.

While a hip brace has been described in detail above, as will be appreciated the coupling 17 may be used in other devices. For example, it may be used in a shoulder brace between portions adapted to be applied to the shoulder and upper arm, respectively, or in braces adapted to be applied to the wrist or ankle, for example.

Instead of using a tensile member such as a threaded stud 46 and nut 48, other releasable clamping or compression applying devices may be employed to exert a compressive force to the outer sides of the washers 49. For example, a stud passing internally through the coupling and having conventional quick disconnect over center cam devices at each end may be employed. Alternatively, an external C clamp or the like bridging externally of the coupling between the outer sides of the washers 49 may be employed.

While the invention has been described with respect to certain preferred embodiments as will be appreciated by those skilled in the art, it is to be understood that the invention is capable of numerous changes, modifications and rearrangements and such changes, modifications and rearrangements are intended to be covered by the following claims.

We claim:

1. A coupling comprising:
   (a) a first portion comprising a collar having an aperture and having a planar bearing surface on an inner side, and a bushing received within the aperture, said bushing having a stub for engaging a first cylindrical recess of a cam member and an inwardly tapering recess therein;
   (b) a second portion comprising a collar having an aperture and having a planar bearing surface on an inner side, and a bushing received within the aperture, said bushing having a stub for engaging a second cylindrical recess of said cam member and an inwardly tapering recess therein;
   (c) said cam member having (i) a first planar bearing face with said first cylindrical recess, said first planar bearing face bearing rotationally on the planar bearing surface of the first portion and journalled thereto through a first journal bearing resisting lateral slippage and (ii) a second planar bearing face with said second cylindrical recess, said second planar bearing face disposed in a plane inclined to the plane of the first planar bearing face and bearing rotationally relative to the planar bearing surface of the second portion and journalled thereto through a second journal bearing resisting lateral slippage; and
   (d) a clamping device urging said bearing surfaces toward said bearing faces of the cam member and generating a frictional reaction retaining each bearing surface in a selected rotational position with respect to the cam member, wherein said clamping device comprising a convex member engaging in each said tapering recess.

2. A coupling according to claims wherein said inwardly tapering recess is conical and said convex member is part spherical.

3. A coupling according to claim 2 wherein said clamping device comprises a tensile stud passing through apertures in said planar bearing surfaces, the cam member and through said journal bearings.

4. An orthotic brace comprising a first brace portion adapted to engage a first body portion of a patient, a second brace portion adapted to engage a second adjacent body portion of the patient, and said first and second brace portions connected to said first and second portions, respectively, of a coupling device according to claim 3.

5. An orthotic brace comprising a first brace portion adapted to engage a first body portion of a patient, a second brace portion adapted to engage a second adjacent body portion of the patient, and said first and second brace portions connected to said first and second portions, respectively, of a coupling device according to claim 2.

6. A coupling according to claim 1 wherein said clamping device comprises a tensile stud passing through apertures in said planar bearing surfaces, the cam member and through said journal bearings.

7. An orthotic brace comprising a first brace portion adapted to engage a first body portion of a patient, a second brace portion adapted to engage a second adjacent body portion of the patient, and said first and second brace portions connected to said first and second portions, respectively, of a coupling device, according to claim 6.

8. An orthotic brace comprising a first brace portion adapted to engage a first body portion of a patient, a second brace portion adapted to engage a second adjacent body portion of the patient, and said first and second brace portions connected to said first and second portions, respectively, of a coupling device according to claim 1.

9. A coupling according to claim 1 wherein said first portion further comprises a first arm adjacent to said collar and the second portion further comprises a second arm adjacent to said collar.

10. A coupling according to claim 9 wherein said arms are connected to said collars.

11. An orthotic brace comprising a first brace portion adapted to engage a first body portion of a patient, a second brace portion adapted to engage a second adjacent body portion of the patient, and said first and second brace portions connected to said first and second portions, respectively, of a coupling according to claim 10.

12. A coupling according to claim 9 wherein said arms are formed integrally with said collars.

13. An orthotic brace comprising a first brace portion adapted to engage a first body portion of a patient, a second brace portion adapted to engage a second adjacent body portion of the patient, and said first and second brace portions connected to said first and second portions, respectively, of a coupling according to claim 12.

14. An orthotic brace comprising a first brace portion adapted to engage a first body portion of a patient, a second brace portion adapted to engage a second adjacent body portion of the patient, and said first and second brace portions connected to said first and second portions, respectively, of a coupling according to claim 9.

15. A coupling comprising:
    (a) a first portion comprising a collar having an aperture and having a planar bearing surface on an inner side, and a bushing received within the aperture, said bushing having a stub for engaging a first cylindrical recess of a cam member and an inwardly tapering recess therein;
    (b) a second portion comprising a collar having an aperture and having a planar bearing surface on an inner side, and a bushing received within the aperture, said bushing having a stub for engaging a second cylindrical recess of said cam member and an inwardly tapering recess therein;
    (c) said cam member having (i) a first planar bearing face with said first cylindrical recess, said first planar bearing face bearing rotationally on the planar bearing surface of the first portion and journalled thereto through a first journal bearing resisting lateral slippage and (ii) a second planar bearing face with said second cylindrical recess, said second planar bearing face disposed in a plane inclined to the plane of the first planar bearing face and bearing rotationally relative to the planar bearing surface of the second portion and journalled thereto through a second journal bearing resisting lateral slippage,
    wherein said second journal bearing comprises a second cam member interposed between and journalled to the first mentioned cam member and to said bearing surface of the second portion, said second cam member having a first planar bearing face with a first cylindrical recess, said first planar bearing face bearing rotationally on the planar bearing surface of said first portion and a second planar bearing face with a second cylindrical recess, said second planar bearing face disposed in a plane inclined to the plane of the first bearing face and bearing rotationally relative to the planar bearing surface of said second portion; and
    (d) a clamping device urging said bearing surfaces toward said bearing faces of the cam members and generating a frictional reaction retaining each bearing surface in a selected rotational position with respect to the cam members, wherein said clamping device comprises a convex member engaging in each said tapering recess.

16. A coupling according to claim 4, wherein said inwardly tapering recess is conical and said convex member is part spherical.

17. A coupling according to claim 16 wherein said clamping device comprises a tensile stud passing through apertures in said planar bearing surfaces, the cam members and through said journal bearings.

18. An orthotic brace comprising a first brace portion adapted to engage a first body portion of a patient, a second brace portion adapted to engage a second adjacent body portion of the patient, and said first and second brace portions connected to said first and second portions, respectively, of a coupling device according to claim 17.

19. An orthotic brace comprising a first brace portion adapted to engage a first body portion of a patient, a second brace portion adapted to engage a second adjacent body portion of the patient, and said first and second brace portions connected to said first and second portions, respectively, of a coupling device according to claim 16.

20. A coupling according to claim 15 wherein said clamping device comprises a tensile stud passing through apertures in said planar bearing surfaces, the cam members and through said journal bearings.

21. An orthotic brace comprising a first brace portion adapted to engage a first body portion of a patient, a second brace portion adapted to engage a second adjacent body portion of the patient, and said first and second brace portions connected to said first and second portions, respectively, of a coupling device according to claim 20.

22. An orthotic brace comprising a first brace portion adapted to engage a first body portion of a patient, a second brace portion adapted to engage a second adjacent body portion of the patient, and said first and second brace portions connected to said first and second portions, respectively, of a coupling device according to claim 15.

23. A coupling according to claim 15 wherein said first portion further comprises a first arm adjacent to said collar and said second portion further comprises a second arm adjacent to said collar.

24. A coupling according to claim 23 wherein said arms are connected to said collars.

25. An orthotic brace comprising a first brace portion adapted to engage a first body portion of a patient, a second brace portion adapted to engage a second adjacent body portion of the patient, and said first and second brace portions connected to said first and second portions, respectively, of a coupling according to claim 24.

26. A coupling according to claim 23 wherein said arms are formed integrally with said collars.

27. An orthotic brace comprising a first brace portion adapted to engage a first body portion of a patient, a second brace portion adapted to engage a second adjacent body portion of the patient, and said first and second brace portions connected to said first and second portions, respectively, of a coupling according to claim 26.

28. An orthotic brace comprising a first brace portion adapted to engage a first body portion of a patient, a second brace portion adapted to engage a second adjacent body portion of the patient, and said first and second brace portions connected to said first and second portions, respectively, of a coupling according to claim 23.

29. An orthotic brace comprising a first brace portion adapted to engage a first body portion of a patient, a second brace portion adapted to engage a second adjacent body portion of the patient, and said first and second brace portions connected to first and second portions, respectively, of a coupling, said coupling comprising:
    (a) said first brace portion comprising a collar having an aperture and having a planar bearing surface on an inner side, and a bushing received within the aperture, said bushing having a stub for engaging a first cylindrical recess of a cam member and an inwardly tapering recess therein;

(b) said second brace portion comprising a collar having an aperture and having a planar bearing surface on an inner side, and a bushing received within the aperture, said bushing having a stub for engaging a second cylindrical recess of said cam member and an inwardly tapering recess therein;

(c) said cam member having (i) a first planar bearing face with said first cylindrical recess, said first planar bearing face bearing rotationally on the planar bearing surface of the first portion and journalled thereto through a first journal bearing resisting lateral slippage and (ii) a second planar bearing face with said second cylindrical recess, said second planar bearing face disposed in a plane inclined to the plane of the first planar bearing face and bearing rotationally relative to the planar bearing surface of the second portion and journalled thereto through a second journal bearing resisting lateral slippage; and (d) a clamping device urging said bearing surfaces toward said bearing faces of the cam member and generating a frictional reaction retaining each bearing surface in a selected rotational position with respect to the cam member to provide the orthotic support, wherein said clamping device comprising a convex member engaging in each said tapering recess.

30. An orthotic brace comprising a first brace portion adapted to engage a first body portion of a patient, a second brace portion adapted to engage a second adjacent body portion of the patient, and said first and second brace portions connected to said first and second portions, respectively, of a coupling according to claim 29 wherein said recess is conical and said convex member is part spherical.

31. An orthotic brace comprising a first brace portion adapted to engage a first body portion of a patient, a second brace portion adapted to engage a second adjacent body portion of the patient, and said first and second brace portions connected to said first and second portions, respectively, of a coupling according to claim 30 wherein said clamping device comprises a tensile stud passing through apertures in said planar bearing surfaces, the cam member and through said journal bearings.

32. An orthotic brace comprising a first brace portion adapted to engage a first body portion of a patient, a second brace portion adapted to engage a second adjacent body portion of the patient, and said first and second brace portions connected to said first and second portions, respectively, of a coupling according to claim 29 wherein said clamping device comprises a tensile stud passing through apertures in said planar bearing surfaces, the cam member and through said journal bearings.

33. An orthotic brace comprising a first brace portion adapted to engage a first body portion of a patient, a second brace portion adapted to engage a second adjacent body portion of the patient, and said first and second brace portions connected to first and second portions, respectively, of a coupling, said coupling comprising:

(a) said first brace portion comprising a collar having an aperture, and having a planar bearing surface on an inner side, and a bushing received within the aperture, said bushing having a stub for engaging a first cylindrical recess of a cam member and an inwardly tapering recess therein;

(b) said second brace portion comprising a collar having an aperture and having a planar bearing surface on an inner side, and a bushing received within the aperture, said bushing having a stub for engaging a second cylindrical recess of said cam member and an inwardly tapering recess therein;

(c) said cam member having (i) a first planar bearing face with said first cylindrical recess, said first planar bearing face bearing rotationally on the planar bearing surface of the first portion and journalled thereto through a first journal bearing resisting lateral slippage and (ii) a second planar bearing face with said second cylindrical recess, said second planar bearing face disposed in a plane inclined to the plane of the first planar bearing face and bearing rotationally relative to the planar bearing surface of the second portion and journalled thereto through a second journal bearing resisting lateral slippage, wherein said second journal bearing comprises a second cam member interposed between and journalled to the first mentioned cam member and to said bearing surface of the second portion, said second cam member having (i) a first planar bearing face with a first cylindrical recess, said first planar bearing face bearing rotationally on the planar bearing surface of said first portion and (ii) a second planar bearing face with a second cylindrical recess, said second planar bearing face disposed in a plane inclined to the plane of the first bearing face and bearing rotationally relative to the planar bearing surface of said second portion; and (d) a clamping device urging said bearing surfaces toward said bearing faces of the cam member and generating a frictional reaction retaining each bearing surface in a selected rotational position with respect to the cam members, wherein said clamping device comprising a convex member engaging in each said tapering recess.

34. An orthotic brace comprising a first brace portion adapted to engage a first body portion of a patient, a second brace portion adapted to engage a second adjacent body portion of the patient, and said first and second brace portions connected to said first and second portions, respectively, of a coupling according to claim 33 wherein said recess is conical and said convex member is part spherical.

35. An orthotic brace comprising a first brace portion adapted to engage a first body portion of a patient, a second brace portion adapted to engage a second adjacent body portion of the patient, and said first and second brace portions connected to said first and second portions, respectively, of a coupling according to claim 34 wherein said clamping device comprises a tensile stud passing through apertures in said planar bearing surfaces, each cam member and through said journal bearings.

36. An orthotic brace comprising a first brace portion adapted to engage a first body portion of a patient, a second brace portion adapted to engage a second adjacent body portion of the patient, and said first and second brace portions connected to said first and second portions, respectively, of a coupling according to claim 33 wherein said clamping device comprises a tensile stud passing through apertures in said planar bearing surfaces, each cam member and through said journal bearings.

\* \* \* \* \*

UNITED STATES PATENT AND TRADEMARK OFFICE
CERTIFICATE OF CORRECTION

PATENT NO. : 6,488,644 B1
DATED : December 3, 2002
INVENTOR(S) : Devin J. Ostrom et al.

It is certified that error appears in the above-identified patent and that said Letters Patent is hereby corrected as shown below:

Column 1,
Line 8, delete "is".

Column 3,
Line 12, delete "land at its base" and insert therefor -- outer bearing face --.

Column 4,
Line 67, delete "a" (first occurrence) and insert therefor -- $\alpha$ --.

Column 5,
Line 1, delete "P" and insert therefor -- $\beta$ --.

Column 6,
Line 25, delete "claims" and insert therefor -- claim 1 --.
Lines 37, 43, 53 and 59, delete "device".

Column 7,
Line 63, delete "4" and insert therefor -- 15 --.

Column 8,
Lines 8, 13, 23 and 29, delete "device".

Column 10,
Line 32, delete "member" and insert therefor -- members --.
Line 35, delete "comprising" and insert therefor -- comprises --.

Signed and Sealed this

Fifth Day of August, 2003

JAMES E. ROGAN
*Director of the United States Patent and Trademark Office*